United States Patent [19]

Lartey et al.

[11] Patent Number: 5,712,253
[45] Date of Patent: Jan. 27, 1998

[54] MACROCYCLIC 13-MEMBERED RING DERIVATIVES OF ERYTHROMYCINS A AND B

[75] Inventors: Paul A. Lartey, Wadsworth, Ill.; Cynthia Burnell Curty, Kenosha, Wis.; Ramin Faghih, Lake Forest, Ill.; Hugh Nerby Nellans, Lake Bluff, Ill.; Albert Christian Petersen, Libertyville, Ill.

[73] Assignee: Abbott Laboratories, Abbott Park, Ill.

[21] Appl. No.: 668,050

[22] Filed: Jun. 18, 1996

[51] Int. Cl.$^6$ .................... A61K 31/70; C07H 17/08
[52] U.S. Cl. .................... 514/28; 514/29; 536/7.1; 536/7.2
[58] Field of Search .................... 536/7.2, 7.1; 514/29, 514/28

[56] References Cited

U.S. PATENT DOCUMENTS

| | | | |
|---|---|---|---|
| 3,878,192 | 4/1975 | Blasima et al. | 536/7.2 |
| 4,640,910 | 2/1987 | Faubl et al. | 514/29 |
| 4,677,097 | 6/1987 | Omura et al. | 514/29 |
| 4,681,872 | 7/1987 | Freiberg et al. | 514/29 |
| 4,833,236 | 5/1989 | Morimoto et al. | 536/7.2 |
| 4,948,782 | 8/1990 | Omura et al. | 514/29 |

FOREIGN PATENT DOCUMENTS

| | | |
|---|---|---|
| 0213617 | 3/1987 | European Pat. Off. . |
| 0215355 | 3/1987 | European Pat. Off. . |
| 0349100 | 1/1990 | European Pat. Off. . |
| 0349100 A | 1/1990 | European Pat. Off. . |

OTHER PUBLICATIONS

Zeitschrift Für Gastroenterologie, vol. 29 (1991), pp. 27–30, H.D. Allescher, "Medikamentöse Beeinflussung der Gastro–Intestinalen Motilität und Sekretion".

Journal of Organic Chemistry, vol. 61, No. 15 (Jul. 1996), pp. 5153–5154, P.A. Lartey et al., "A Novel 13–Membered Erythromycin Analog via Dast–Induced Ring Contraction".

Tsuzuki, K., "Motilides, Macrolides with Gastrointestinal Motor Stimulating Activity[1] 1. O–Substituted and Tertiary N–Substituted Derivatives of 8,9–Anhydroerythromycin A 6,9–Hemiacetal", *Chem. Pharm. Bull.*, vol. 37, No. 10, Oct., 1989, pp. 2687–2700.

*Primary Examiner*—Elli Peselev
*Attorney, Agent, or Firm*—Mona Anand

[57] ABSTRACT

Novel macrocyclic 13-membered ring-contracted compounds derived from erythromycins A and B having the Formula (I)

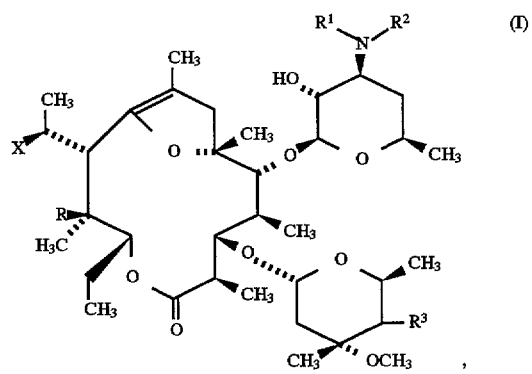

and pharmaceutically acceptable salts thereof, wherein R, $R^1$, $R^2$, $R^3$ and X are specifically defined, having use in treating gastrointestinal disorders associated with hypermotilinemia, pharmaceutical compositions thereof, a method of treating gastrointestinal disorders associated with hypermotilinemia with said pharmaceutical compositions, and processes for the preparation thereof.

12 Claims, No Drawings

MACROCYCLIC 13-MEMBERED RING DERIVATIVES OF ERYTHROMYCINS A AND B

TECHNICAL FIELD

This invention relates to novel ring-contracted 13-membered ring derivatives of erythromycins A and B, pharmaceutical compositions containing these compounds, a method of treating gastrointestinal disorders related to hypermotilinemia with pharmaceutical compositions containing these compounds, and a process for their preparation.

BACKGROUND OF THE INVENTION

The primary function of the alimentary or gastrointestinal (GI) tract is to provide the body with a balanced supply of water, electrolytes and nutrients. In order for this to be achieved, food must be moved along the GI tract at an appropriate rate for digestion, absorption and secretion to take place. Food is normally transported through the GI tract in a well-coordinated manner by propulsive movements which are mediated by clusters of smooth muscle contractions in a process commonly referred to as peristalsis.

Normal GI tract function is mediated by a number of naturally occurring factors including the hormone, motilin, which is a 22 amino acid peptide. The role of motilin is to effect coordinated propulsive contractions of the GI tract, starting from the esophagus, radiating through the stomach and propagating through the intestines. The objective of these propulsive contractions is to move food which has been digested in the stomach, through the GI tract, this process being referred to as the migrating motor complex. Motilin also causes pancreatic secretion, leading to release of pancreatic factors and hormones also involved in the digestion, absorption and storage of nutrients derived from food. In the fasting state, motilin is periodically released, resulting in the induction of propulsive contractile activity, known as Phase III of the myoelectric motor complex (MMC). The induction of MMC is said to create the sensation of hunger and may be associated with a person's desire to eat.

While the ordered natural release of motilin by the body is beneficial, in certain disease states, any defect in the normal motility pattern of GI tract can lead to the development of a number of indications.

For example, an incompetent or weak lower esophageal sphincter may result in frequent reflux of ingested food from the stomach into the esophagus which may lead to esophagitis. Prokinetic agents (also called motility-enhancing agents) are useful in treating reflux esophagitis because they (a) increase the pressure of the lower esophageal sphincter, thereby inhibiting reflux; (b) increase the force of esophageal peristalsis to facilitate clearance of food from the esophagus into the stomach; and (c) increase gastric emptying, thereby further decreasing the mass available for reflux.

On the other hand, excessive release of motilin, or hypersensitization of motilin receptors, may lead to uncoordinated and excessive stimulation of GI tract contractions and can lead to a number of conditions. Some of these are gastrointestinal dumping syndrome, atrophic gastritis, pancreatitis, diarrhea, irritable bowel syndrome, Crohn's disease, ulcerative colitis and celiac disease. Antagonists of motilin may be utilized to treat or prevent the symptoms associated with hypermotilinemia and hypersensitization of motilin receptors. In addition, administration of a motilin antagonist may result in the blockade of hunger sensations, thereby creating a feeling of satiety.

Macrocyclic lactone (macrolide) prokinetic agents are known. For example, J. S. Gidda et al., in European Patent Application No. 0349100, published Jan. 3, 1990, disclose 12-membered macrolides for use as gastrointestinal motility enhancers. S. Omura and Z. Itoh, in U.S. Pat. No. 4,677,097, issued Jun. 30, 1987, European Application No. 215,355, published Mar. 25, 1987, and European Application No. 213,617, published Mar. 11, 1987, disclose derivatives of erythromycins A, B, C and D which are useful as stimulants of digestive tract contractile motion. Additionally, T. Sunazuka, et al., Chem. Pharm. Bull. 37(10): 2701–2709 (1989) disclose quaternary derivatives of 8,9-anhydroerythromycin A 6,9-hemiacetal and 9,9-dihydroerythromycin A 9-epoxide with gastrointestinal motor stimulating Macrocyclic lactone (macrolide) prokinetic agents are known. For example, R. Faghih et al, in PCT Application WO 9312780, published Jul. 22, 1993, disclose 4"-deoxyerythromycin compounds for use in enhancing gastrointestinal motility, and J. S. Gidda et al., in European Patent Application No. 0349100, published Jan. 3, 1990, disclose 12-membered macrolides also for use as gastrointestinal motility enhancing activity.

However, none of the above references disclose derivatives which possess motilin antagonist activity. Therefore, there exists a need for compounds which would be useful as antagonists of motilin and can also be used in the treatment of obesity.

SUMMARY OF THE INVENTION

In one aspect of the present invention, are provided macrocyclic 13-membered ring compounds derived from erythromycins A and B having the Formula (I)

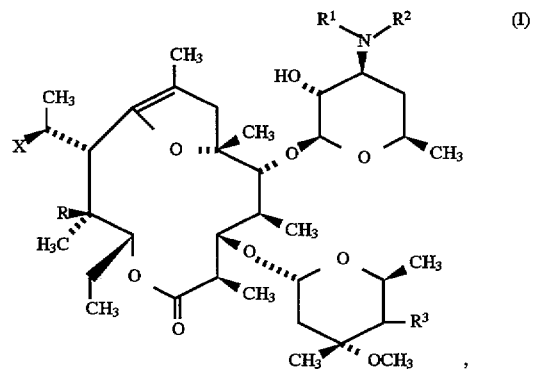

and pharmaceutically acceptable salts thereof.

In Formula (I),

R is H or OH;

$R^1$ and $R^2$ are independently selected from the group consisting of H, $C_1$–$C_8$-alkyl, phenyl-$C_1$–$C_8$-alkyl, and naphthyl-$C_1$–$C_8$-alkyl;

$R^3$ is selected from the group consisting of H, OH, O—$C_1$–$C_8$-alkyl, O—CO—$C_1$–$C_8$-alkyl, O—CO-phenyl, O—CO—$NR^4R^5$, where $R^4$ and $R^5$ are independently H or $C_1$–$C_8$-alkyl; $NH_2$; N—CO—$C_1$–$C_8$-alkyl; N—CO-phenyl; and N—CO—$NR^4R^5$, wherein $R^4$ and $R^5$ are independently H or $C_1$–$C_8$-alkyl; and X is selected from the group consisting of F, Cl, Br, or I.

These novel 13-membered ring-contracted erythromycin A and B compounds of the present invention are useful as motilin antagonists and in the treatment of gastrointestinal disorders, especially those associated with hypermotilinemia such as: gastrointestinal dumping syndrome, atrophic gastritis, pancreatitis, diarrhea, irritable bowel syndrome, Crohn's disease, ulcerative colitis, celiac disease, and obesity.

In another aspect of the invention are provided pharmaceutical compositions containing compounds of Formula (I).

Another aspect of the invention is a method for treating gastrointestinal disorders related to hypermotilinemia with pharmaceutical compositions containing these compounds.

In yet other aspects of the invention are provided processes for the preparation of the compounds of Formula (I).

DETAILED DESCRIPTION OF THE INVENTION

In a preferred embodiment of the invention are compounds of Formula (I) wherein $R^1$ and $R^2$ are $C_1$–$C_8$-alkyl and $R^3$ is H, OH, O—$C_1$–$C_8$-alkyl, O—CO—$NR^4R^5$, where $R^4$ and $R^5$ are independently H or $C_1$–$C_8$-alkyl, and $NH_2$.

In a more preferred embodiment of the invention are compounds of Formula (I) wherein R is H; $R^1$ and $R^2$ are $C_1$–$C_8$-alkyl, $R^3$ is H and X is F.

Representative compounds of the invention include:

Compound of Formula (I); R=H; $R^1$=methyl; $R^2$=ethyl; $R^3$=H; X=F;

Compound of Formula (I); R=H; $R^1$=methyl; $R^2$=H; $R^3$=H; X=F;

Compound of Formula (I); R=OH; $R^1$=methyl; $R^2$=ethyl; $R^3$=H; X=F;

Compound of Formula (I); R=H; $R^1$=methyl; $R^2$=i-propyl; $R^3$=H; X=F;

Compound of Formula (I); R=H; $R^1$=methyl; $R^2$=phenylmethyl; $R^3$=H; X=F;

Compound of Formula (I); R=H; $R^1$=methyl; $R^2$=methyl; $R^3$=OH; X=F;

Compound of Formula (I); R=H; $R^1$=methyl; $R^2$=methyl; $R^3$=methoxy; X=F;

Compound of Formula (I); R=H; $R^1$=methyl; $R^2$=methyl; $R^3$=OCON$(CH_3)_2$; X=F;

Compound of Formula (I); R=H; $R^1$=methyl; $R^2$=methyl; $R^3$=$NH_2$; X=F; and Compound of Formula (I); R=H; $R^1$=methyl; $R^2$=methyl; $R^3$=H; X=Cl;

or a pharmaceutically acceptable salt thereof.

A preferred compound of the invention is the compound having the formula which is a compound of Formula (I) wherein R=H; $R^1$=methyl; $R^2$=ethyl; $R^3$=H; and X=F; or a pharmaceutically acceptable salt thereof.

In another aspect of the invention is provided a process for the preparation of the compounds having the formula wherein R is H or OH;

$R^1$ and $R^2$ are independently selected from the group consisting of H, $C_1$–$C_8$-alkyl, phenyl-$C_1$–$C_8$-alkyl, and naphthyl-$C_1$–$C_8$-alkyl;

$R^3$ is selected from the group consisting of H, OH, O—$C_1$–$C_8$-alkyl, O—CO—$C_1$–$C_8$-alkyl, O—CO—phenyl, O—CO—$NR^4R^5$, where $R^4$ and $R^5$ are independently H or $C_1$–$C_8$-alkyl; $NH_2$; N—CO—$C_1$–$C_8$-alkyl; N—CO-phenyl; N—CO—$NR^4R^5$, wherein $R^4$ and $R^5$ are independently H or $C_1$–$C_8$-alkyl; and X is selected from the group consisting of F, Cl, Br, or I; the method comprising (a) selectively protecting the 2'-hydroxyl group of a compound having the formula wherein $R^3$ is as described above, by treatment with a reagent selected from the group comprising an acid anhydride and an acid halide under neutral aprotic conditions, and isolating the first intermediate compound having the formula

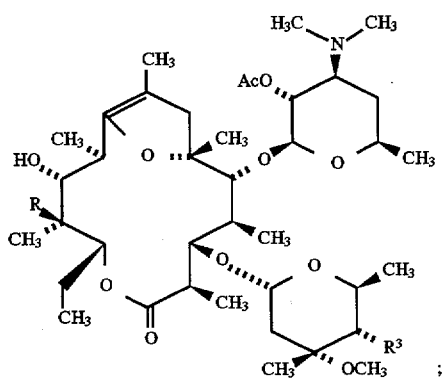

(b) ring-contracting the first intermediate compound by treatment with a reagent capable of donating a nucleophilic halogen species, at ambient temperature and under an inert atmosphere, and isolating the 13-membered ring-contracted second intermediate compound having the formula

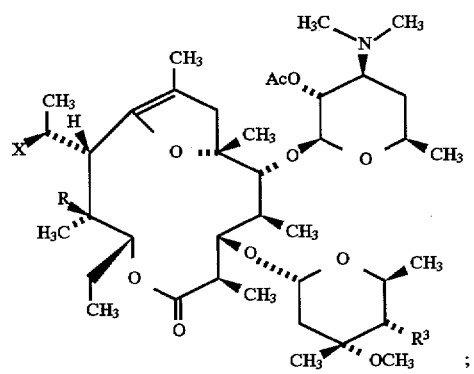

(c) optionally demethylating one or more of the 3'-N methyl groups by treatment with iodine in the presence of sodium acetate in a methanolic solution, followed by N-alkylation by treatment with a reagent selected from the group comprising an alkyl halide and hydrogen and a noble metal catalyst in the presence of an aldehyde or ketone and an alkali metal halide, and isolating the third intermediate compound having the formula

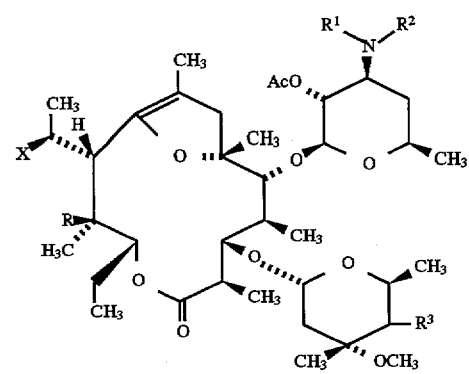

(d) deprotecting the 2'hydroxyl protecting group by treatment with methanol and isolating the desired product.

In a preferred embodiment of the process described above, X is F and in step (b) the reagent capable of donating a nucleophilic halogen species is diethylamidosulfur trifluoride (DAST).

In another aspect of the invention is the process for the preparation of the compound having the formula

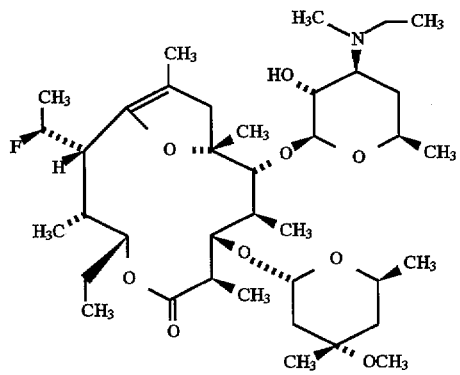

the method comprising (a) treating the compound having the formula

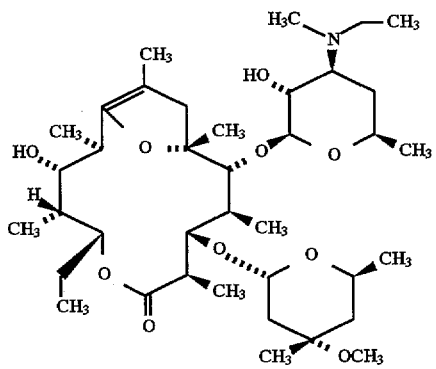

with acetic anhydride under $N_2$ at room temperature for 4 hours, and isolating the first intermediate compound having the formula

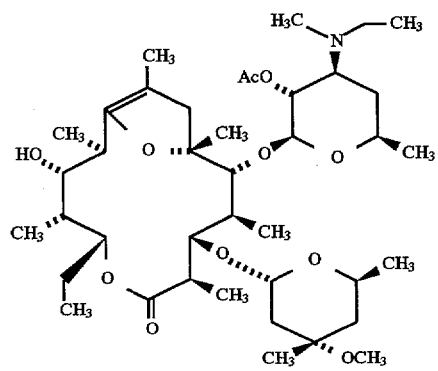

(b) ring-contracting the first intermediate compound by treatment with diethylamidosulfur trifluoride (DAST) under $N_2$ at room temperature for 4 hours, and isolating the second intermediate compound having the formula

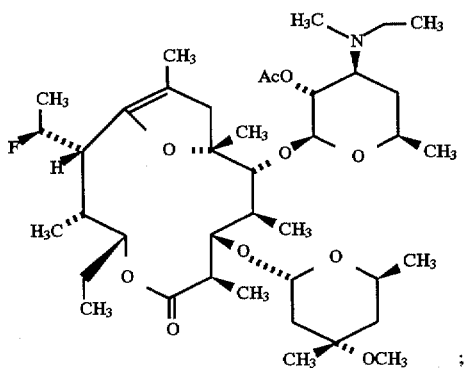

(c) treating the second intermediate compound with methanol, and isolating the desired product.

The term "$C_1$–$C_8$-alkyl" as used herein refers to a $C_1$–$C_8$-alkyl straight or branched chain saturated hydrocarbon radical including, but not limited to, methyl, ethyl, n-propyl, isopropyl, n-butyl, sec-butyl, isobutyl, tert-butyl, hexyl, heptyl, octyl and the like.

The term "naphthyl-$C_1$–$C_8$-alkyl" refers to $C_1$–$C_8$-alkyl group as defined above substituted by a naphthyl moiety by replacement of one of the hydrogen atoms on the alkyl moiety.

The term "phenyl-$C_1$–$C_8$-alkyl" refers to $C_1$–$C_8$-alkyl group as defined above substituted by a phenyl moiety by replacement of one of the hydrogen atoms on the alkyl moiety.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis.*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "atrophic gastritis" refers to the wasting and inflammation of the GI tract due to hormonal changes.

The term "celiac disease" refers GI tract abnormalities resulting from sensitivity to gluten.

The term "Crohn's disease" refers to inflammation of the small bowel.

The term "diarrhea" refers to abnormal discharge of fluid fecal mater from the bowel.

The term "gastrointestinal dumping syndrome" refers to the passage of partially undigested food through the GI tract.

The term "irritable bowel syndrome" refers to uncoordinated spastic motility of the GI tract.

The term "pancreatitis" refers to inflammation of the pancreas.

The term "ulcerative colitis" refers to inflammation of the colon.

By "pharmaceutically acceptable salts" is meant those acid addition salts of the compounds of Formula (I) which are, within the scope of sound medical judgment, suitable for use in contact with the tissues of humans and lower animals without undue toxicity, irritation, allergic response, and the like commensurate with a reasonable benefit/risk ratio, and which are effective for their intended use.

Pharmaceutically acceptable salts are well known in the art. For example, S. M. Berge, et al. describe pharmaceutically salts in detail in *J. Pharmaceutical Sciences* (1977), 66: 1–19. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptonate, hexanoate, 2-naphthalenesulfonate, pamoate, persulfate, pivalate, propionate, undecanoate salts and the like, and may be prepared according to conventional methods. Representative alkali or alkaline earth metal salts include sodium, calcium, potassium, magnesium salts and the like. Pharmaceutically acceptable counterions for the quaternary ammonium salt compounds formed when $R^4$ is present include halide (especially bromide and iodide), hydroxide, carboxylate, sulfate, phosphate, nitrate, lower-alkyl sulfonate and arysulfonate.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

By a "therapeutically effective amount" of a compound of the invention is meant a sufficient amount of the compound to treat a gastrointestinal disorder, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, of from about 0.0001 to about 25 mg/kg body weight. More preferably, daily doses may range from about 0.0005 to about 10 mg/kg or, even more preferably, from about 0.005 to about 2 mg/kg body weight. Single dose compositions may contain such amounts or submultiples thereof as make up the daily dose. In general, treatment regimens according to the present invention comprise administration to a human patient in need of such treatment of from about 1 mg to about 100 mg of the compound(s) of this invention per day in multiple doses or in a single dose.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants such as wetting agents; emulsifying or suspending agents and sweetening, flavoring or perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, as for example in solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulation can be sterilized, as for example by filtration through a bacteria-retaining filter or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, as for example, its crystal size and crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions which are compatible with body tissues.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be combined in microencapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Further improvements in the delivery of the compounds of the invention may be accomplished by the formation of biolabile derivatives, or prodrugs, which upon administration to a patient are converted in vivo to the parent compound. Prodrugs are well-known in the art, and may be prepared by the addition, as for example by esterification or other derivatization at the 2' position of the present compounds, of a pharmaceutically acceptable and biologically cleavable group. (A thorough discussion of prodrugs is provided in T. Higuchi and V. Stella, "Pro-drugs as Novel Delivery Systems", Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.) It is expected that such prodrugs will be readily apparent to the skilled reader and will be regarded as functional equivalents of the compounds of the invention.

SYNTHETIC METHODS

The compounds and processes of the present invention will be better understood in connection with the following synthetic schemes which illustrate the methods by which the compounds of the invention may be prepared. The groups R, $R^1$, $R^2$, $R^3$ and X are as defined with respect to Formula (I) above unless otherwise noted below.

In accordance with Scheme 1 below, compounds (1) are selectively protected at the 2'-hydroxyl by treatment with an acid anhydride, such as acetic anhydride, for example, under neutral aprotic conditions, such as in methylene chloride or ethyl acetate, or by treatment with an acyl halide, such as acetyl chloride under similar conditions, to prepare the 2'-hydroxy protected compound (2). The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991).

The starting material compounds (1) are 8,9-anhydro-6,9-hemiacetal derivatives of erythromycin A (R=OH) or B (R=H), and may be prepared according to published procedures (Kurath et al., *Experientia*, 27:362–363 (1971). In the case wherein the final compound of formula (I) is desired to have $R^1$ or $R^2$=hydrogen, the demethylation reaction is carried out near or as the last step of the procedure in order to protect the nitrogen atom from reacting with other reagents. Starting materials wherein $R^3$ are 4" hydroxy derivatives, such as esters, carbamates, and the like, may be prepared by methods standard in the erythromycin chemical art. Starting materials wherein $R^3$ are 4"-deoxy compounds may be prepared by the methods of Lartey et al., *J. Med. Chem.*, 38:1793–1798 (1995). Starting materials wherein $R^3$ are amino derivatives may be prepared by the methods described by L. A. Freiberg, et al., 29th Interscience Conference on Antimicrobial Agents and Chemotherapy (Houston, Tex.), 1029 (1989).

The desired combinations of $R^1$, $R^2$ and $R^3$ may be achieved by combination or sequential treatment of a precursor under appropriate reaction conditions (as described herein or in the cited references). Furthermore, an alternative route to the preparation of the desired compounds may begin with replacement of the N-methyl groups with such other alkyl groups ($R^1$ and $R^2$) as may be desired, followed by 2-hydroxy protection and subsequent reactions as described below.

The 2'-hydroxy protected compound (2) is then dissolved in an aprotic solvent, such as methylene chloride, and treated with a reagent capable donating a nucleophilic halogen species, such as diethylamidosulfur trifluoride (DAST) at ambient temperature and under an inert atmosphere. This reaction induces ring contraction to afford a 13-membered ring-contracted erythromycin compound (3) (newly named a dodecalide), with concomitant introduction of halogen onto the carbon atom formerly in the ring (the carbon to which the X group is attached in compound (3)).

SCHEME 1

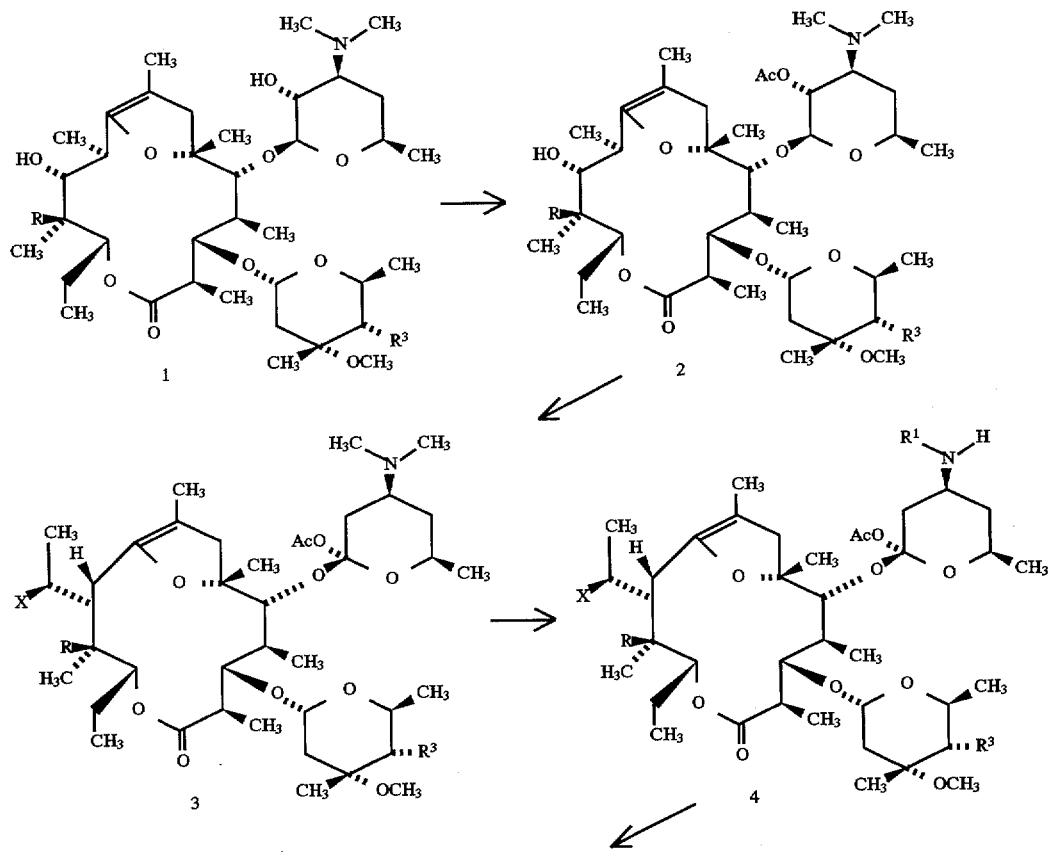

-continued
SCHEME 1

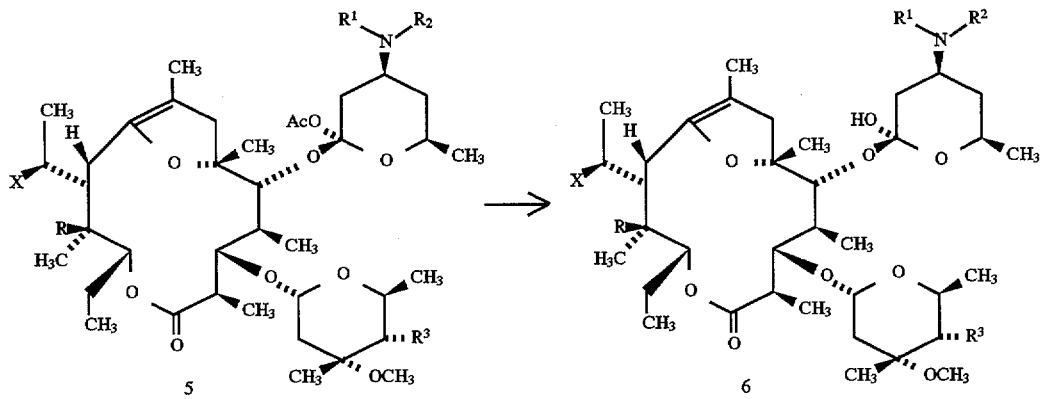

If it is desired to replace the 3'-N-methyl groups of compound (3), it is dissolved in methanol and treated with iodine in presence of sodium acetate to remove one or more of the 3'-N-methyl groups. The N-demethylated compound (4, $R^1$=H) or the singly demethylated compound (4, $R^1$=CH$_3$) may subsequently be alkylated either using an alkyl halide, by reductive alkylation with an aldehyde or ketone in the presence of an alkali metal hydride, or by reductive alkylation with an aldehyde or ketone by catalytic hydrogenation to prepared the desired compound (5).

Treatment of compound (5) with methanol to remove the acetyl group (2'-hydroxy protecting group) gives compound (6), which is a compound of Formula (I) wherein R, $R^1$, $R^2$, $R^3$ and X are as desired.

SCHEME 2

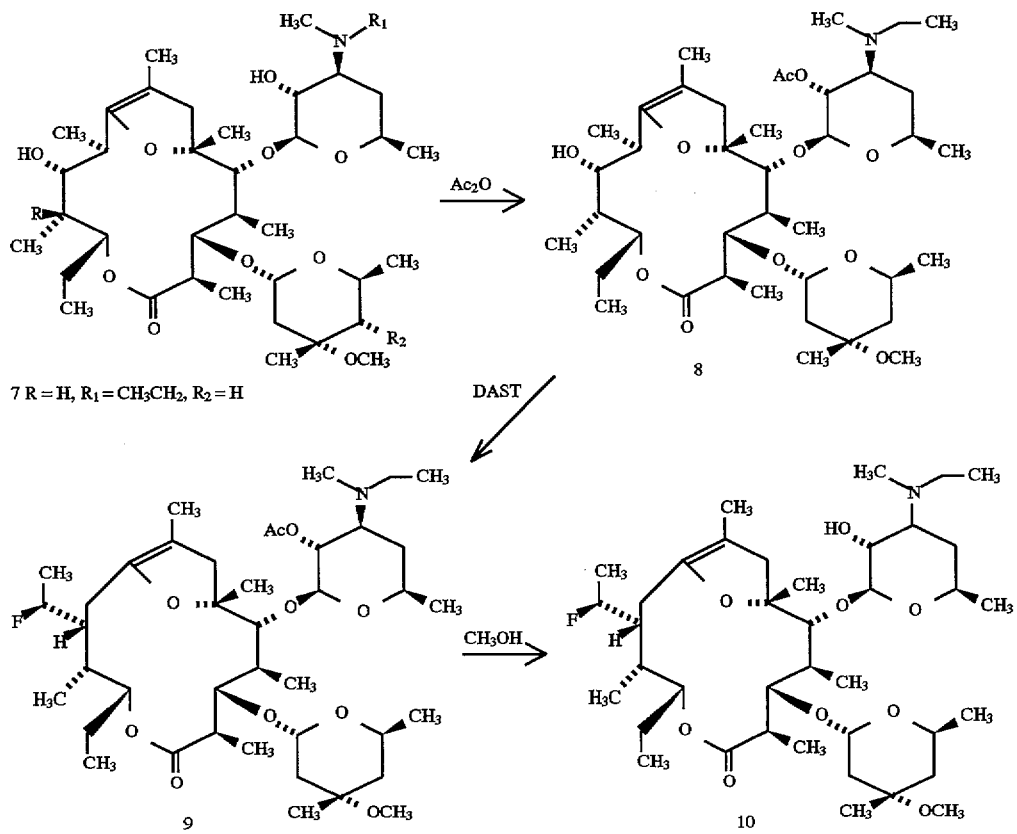

Scheme 2 illustrates a specific alternate process in which the $R^1$ and $R^2$ groups are selected and modified before the ring contraction is performed. Compound 7 (prepared as described in Example 5 of PCT Application WO 9312780, published Jul. 22, 1993) is treated with acetic anhydride under N$_2$ at room temperature for 4 hours to prepare compound (8). Compound (8) is treated with DAST under $N_2$ at room temperature for 4 hours to prepare compound (9). Compound (9) is stirred in methanol overnight to afford compound (10).

EXAMPLES

The foregoing schemes may be better understood by reference to the following examples, which are provided for illustration only and are not intended as a limitation of the invention.

EXAMPLE 1

Compound of Formula (I); R=H; $R^1$=methyl; $R^2$=ethyl; $R^3$=H; X=F

Step 1a. Compound (8) of Scheme 2

The compound (7) of Scheme 2 (3.01 g, 4.31 mmol, prepared as described in Example 5 of PCT Application WO 9312780, published Jul. 22, 1993) was dissolved in $CH_2Cl_2$ (23 mL). Acetic anhydride (0.8 mL, 8.5 mmol) was added via syringe and the mixture stirred under $N_2$ for 4 hours at room temperature. The mixture was diluted with $CH_2Cl_2$ (150 mL) and extracted sequentially with saturated $NaHCO_3$, $H_2O$, and brine (40 mL each). The organic phase was dried over $Na_2SO_4$ and solvent removed in vacuo to give a solid which was purified by chromatography to afford 2.60 g (81%) of the title compound: $[a]_D$–30.0 (c 1.0, $CHCl_3$); $^1H$ NMR ($CDCl_3$) d 0.84 (d, 3H, J=12.5), 0.90 (t, 3H, J=12.5, 12.5), 0.96 (d, 3H, J=13.0), 1.01 (t, 3H, J=11.8, 11.8), 1.06 (d, 3H, J=11.5), 1.15 (s, 3H), 116 (d, 3H, J=12.0), 1.17 (d, 3H, J=9.0), 1.18 (d, 3H, J=10.0), 1.25–1.54 (m, 4H), 1.34 (s, 3H), 1.56 (s, 3H), 1.68 (m, 4H), 1.93 (m, 3H), 2.0 (s, 3H), 2.24 (s, 3H), 2.25–2.80 (m, 7H), 3.32 (s, 3H), 3.42 (m, 1H), 3.62 (m, 1H), 3.82 (d, 1H, J=11.0), 4.0 (m, 1H), 4.34 (m, 1H), 4.65 (m, 2H), 5.15 (m, 1H), 5.19 (d, 1H, J=7.0); $^{13}C$-NMR ($CDCl_3$) d 8.7, 10.4, 11.9, 13.3, 14.1, 14.4, 21.1, 21.4, 21.7, 25.0, 25.4, 26.4, 31.9, 33.3, 33.6, 36.7, 42.1, 42.7, 43.0, 44.5, 45.9, 47.9, 49.2, 61.4, 62.3, 67.8, 70.7, 71.9, 76.8, 77.2, 80.0, 85.7, 95.6, 100.2, 101.4, 151.5, 169.9, 178.2; MS m/e 740 (M+H+); Analysis Calculated for $C_{40}H_{69}NO_{11}$: C, 64.92; H, 9.39; N, 1.89. Found: C, 64.97; H, 9.79; N, 2.12.

Step. 1b. Compound (9) of Scheme 2

The compound from step 1a (0.50 g, 0.68 mmol) was dissolved in $CH_2Cl_2$ (20 mL). DAST (0.3 mL, 2.27 mmol) was added via syringe. The mixture was stirred at room temperature and under $N_2$ for 4 h, diluted with $CH_2Cl_2$ (50 mL) and extracted sequentially with saturated $NaHCO_3$, $H_2O$ and brine (10 mL each). The organic phase was dried over $Na_2SO_4$ and solvent removed in vacuo to give a mixture which was purified by chromatography to afford 0.37 g (73%) of the title compound: $[a]_D$–24.1° (c 0.9, $CHCl_3$); $^1H$ NMR ($CDCl_3$) d 0.80 (t, 3H, J=7.5, 7.5), 0.85 (d, 3H, J=8.0), 0.88 (d, 3H, J=7.5), 0.94 (t, 3H, J=7.5, 7.5), 1.09 (d, 3H, J=7.5), 1.10 (s, 3H), 1.12 (d, 3H, J=6.0), 1.19 (d, 3H, J=6.0), 1.25 (m, 3H), 1.30 (s, 3H), 1.32 (dd, 3H, J=5.5, 24.3), 1.36 (m, 2H), 1.50 (s, 3H), 1.60 (m, 3H), 1.85 (d, 1H, J=16.5), 1.98 (m, 1H), 1.99 (s, 3H), 2.15 (s, 3H), 2.24 (dd, 1H, J=7.5, 14.8), 2.30 (m, 2H), 2.48 (m, 1H), 2.55 (m, 1H), 2.64 (m, 1H), 2.75 (d, 1H, J=15), 3.22 (s, 3H), 3.40 (m, 1H), 3.58 (d, 1H, J=8.5), 3.88 (m, 1H), 4.20 (m, 1H), 4.45 (d, 1H, J=8.0), 4.59 (m, 1H), 4.70 (m, 2H), 4.80 (m, 1H), 4.86 (d, 1H, J=4.5); $^{13}C$-NMR ($CDCl_3$) d 9.4, 9.4, 10.2, 13.0, 13.6, 14.1, 19.5, 19.8, 21.1, 21.4, 21, 25.5, 25.6, 27.0, 31.9, 33.9, 34.0, 34.1, 36.7, 42.5, 44.2, 45.7, 47.9, 49.4, 52.2, 52.5, 61.1, 62.5, 68.4, 70.7, 71.5, 77.3, 81.4, 82.2, 86.2, 88.9, 91.1, 96.5, 101.2, 146.0, 146.2, 169.9, 177.2; MS m/e 742 (M+H+); Analysis Calculated for $C_{40}H_{68}F NO_{10}$: C, 64.75; H, 9.23; N, 1.88. Found: C, 64.81; H, 9.48; N, 1.75.

Step 1c. Compound of Formula (I); R=H; $R^1$=methyl; $R^2$=ethyl; $R^3$=H; X=F (Compound (10) of Scheme 2)

The compound from step 1b (0.072 g, 0.097 mmol) was dissolved in $CH_3OH$ (10 mL) and the mixture stirred overnight at room temperature. Solvent was removed in vacuo and the residue chromatographed to afford 0.06 g (90%) of 7: $[a]_D$–20.5° (c 0.9, $CHCl_3$); $^1H$ NMR ($CDCl_3$) d 0.88 (t, 3H, J=7.5, 7.5), 1.00 (d, 3H, J=6.5), 1.08 (t, 3H, J=3.5, 3.5), 1.09 (d, 3H, J=7.5), 1.12 (d, 3H, J=7.5), 1.14 (s, 3H), 1.19 (d, 3H, J=6.5), 1.20 (d, 3H, J=6.0), 1.26 (s, 1H), 1.32 (m, 1H), 1.36–1.47 (m, 8H), 1.59 (s, 3H), 1.64 (m, 1H), 1.65 (m, 1H), 1.76 (m, 1H), 1.96 (d, 1H, J=15.5), 2.08 (m, 1H), 2.24 (s, 4H), 2.33–2.38 (m, 2H), 2.43 (dd, 1H, J=10.5, 15.3), 2.50–2.64 (m, 3H), 2.97 (d, 1H, J=16.5), 3.21 (m, 1H), 3.28 (s, 3H), 3.51 (m, 1H), 3.70 (d, 1H, J=8.0), 4.00 (m, 1H), 4.31 (m, 1H), 4.45 (d, 1H, J=7.0), 4.64–4.95 (m, 3H); $^{13}C$-NMR ($CDCl_3$) d 9.0, 9.4, 10.2, 12.9, 13.6, 13.9, 19.5, 19.8, 21.3, 21.6, 25.4, 25.6, 27.1, 29.8, 33.8, 34.0, 34.1, 36.2, 42.8, 44.2, 45.7, 45.7, 47.6, 49.4, 52.3, 52.5, 61.1, 64.7, 68.8, 70.4, 70.6, 77.2, 81.5, 82.2, 86.2, 88.9, 91.2, 96.5, 103.3, 104.1, 146.1, 146.2, 177.3; MS m/e 700 (M+H+); Analysis Calculated for $C_{38}H_{66}FNO_9 \cdot 2H_2O$: C, 62.01; H, 9.58; N, 1.90. Found: C, 62.24; H, 9.21; N, 1.75.

Examples 2–10

Following the procedures of Example 1, substituting for the starting material of step 1a the appropriately substituted starting material (wherein R, $R^1$, $R^2$ and $R^3$ are as described in Table 1 below, the compounds having the formula

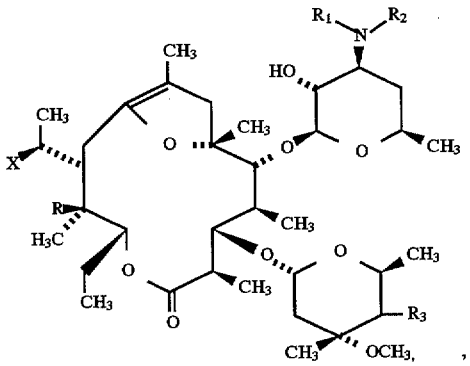

wherein R, $R^1$, $R^2$ and $R^3$ are as described in Table 1, are prepared.

TABLE 1

| Ex. No. | X | R | $R_1$ | $R_2$ | $R_3$ | Name |
|---|---|---|---|---|---|---|
| 2 | F | H | $CH_3$ | H | H | Compound of Formula (I); R = H; $R^1$ = methyl; $R^2$ = H; $R^3$ = H; X = F |
| 3 | F | OH | $CH_3$ | $C_2H_5$ | H | Compound of Formula (I); R = OH; $R^1$ = methyl; $R^2$ = ethyl; $R^3$ = H; X = F |
| 4 | F | H | $CH_3$ | $CH(CH_3)_2$ | H | Compound of Formula (I); R = H; $R^1$ = methyl; $R^2$ = i-propyl; $R^3$ = H; X = F |

TABLE 1-continued

| Ex. No. | X | R | $R_1$ | $R_2$ | $R_3$ | Name |
|---|---|---|---|---|---|---|
| 5 | F | H | $CH_3$ | $CH_2Ph$ | H | Compound of Formula (I); R = H; $R^1$ = methyl; $R^2$ = phenylmethyl; $R^3$ = H; X = F |
| 6 | F | H | $CH_3$ | $CH_3$ | OH | Compound of Formula (I); R = H; $R^1$ = methyl; $R^2$ = methyl; $R^3$ = OH; X = F |
| 7 | F | H | $CH_3$ | $CH_3$ | $OCH_3$ | Compound of Formula (I); R = H; $R^1$ = methyl; $R^2$ = methyl; $R^3$ = methoxy; X = F |
| 8 | F | H | $CH_3$ | $CH_3$ | OCON$(CH_3)_2$ | Compound of Formula (I); R = H; $R^1$ = methyl; $R^2$ = methyl; $R^3$ = OCON$(CH_3)_2$; X = F |
| 9 | F | H | $CH_3$ | $CH_3$ | $NH_2$ | Compound of Formula (I); R = H; $R^1$ = methyl; $R^2$ = methyl; $R^3$ = $NH_2$; X = F |
| 10 | Cl | H | $CH_3$ | $CH_3$ | H | Compound of Formula (I); R = H; $R^1$ = methyl; $R^2$ = methyl; $R^3$ = H; X = Cl |

Example 11

BIOLOGICAL ACTIVITY IN VITRO PROKINETIC AND ANTIBACTERIAL ACTIVITIES

In Vitro Prokinetic Activity

The compounds of the present invention were tested in vitro for their ability to induce contraction of smooth muscle strips isolated from rabbit small intestine using the following procedure:

Rabbits were sacrificed and 15 cm of duodenum was rapidly removed and placed in ice-cold modified Ringers solution (120 mM sodium chloride, 25 mM sodium bicarbonate, 4.7 mM potassium chloride, 1.25 mM calcium chloride, 1.20 mM magnesium sulfate and 5.6 mM glucose). The longitudinal muscle layer was separated from the circular muscle by blunt dissection and cut into strips of 10×20 mm. Double-folded strips were vertically suspended between two hooks in 10 mL tissue baths with a mechanical preload of 1 g. The upper hook was connected to an isotonic force transducer, and its displacement was recorded on a Grass polygraph. The tissue baths contained modified Ringers solution at 37° C. and were continuously gassed with 95% oxygen/5% carbon dioxide in order to maintain the pH at 7.5.

After a stabilization period of at least 60 minutes, a contractility dose-response series was performed by adding increasing final concentrations of methacholine ($10^{-7}$M, $10^{-6}$M and $10^{-5}$M) in volumes of 100 µL. The bath solutions were replaced at least three times between doses.

After the methacholine dose-response series was completed, a test compound dose response curve was initiated by the same procedure used for the methacholine dose-response series, with at least five concentrations of test compound within the range of $10^{-10}$M to $10^{-4}$M. The tissues were washed repeatedly between doses, and the studies were completed by recording the contractile response to $10^{-5}$M methacholine to ascertain integrity of the muscle preparation. Contractile responses were expressed as percent of maximal methacholine induced contraction. The concentration of test compound which produces half of the maximal contraction ($ED_{50}$ value) and the negative logarithm of the $ED_{50}$ value ($pED_{50}$) were estimated from the dose-response curves. The $pED_{50}$ values were compared to motilin, ($pED_{50}$: 8.10) a known gastrointestinal prokinetic agent.

The compound of Example 1 was found to be a very weak agonist for induction of contractile activity in rabbit duodenal smooth muscle preparation: $pED_{50}$<4.0, more than four orders of magnitude less potent than motilin.

Antibacterial Activity

Compounds of the invention were next tested for antibacterial potency, such activity being regarded as an undesirable side effect of motilin antagonist therapy. Assays were conducted using methodology well-known in the art (the agar dilution method). As illustrated by the data shown in Table 2, below, the compounds were found to have very low antibacterial potency, thus further distinguishing them from typical erythromycin antibiotics.

TABLE 2

SELECTED MIC DATA

| Organism | Strain | MIC of Example 1 | MIC of Erythromycin |
|---|---|---|---|
| Streptococcus aureus | ATCC 7538P | 50 | 0.2 |
| Streptococcus aureus | A5177 | 50 | 6.2 |
| Streptococcus bovis | ATCC 8043 | 25 | 0.05 |
| Streptococcus pyogenes | EES61 | 25 | 0.05 |
| Escherichia coli | SS | >100 | 0.39 |
| Pseudomonas eruginosa | K799/WT | >100 | 0.78 |

Motilin Receptor Binding Activity

Binding affinity for motilin receptors was determined according to the protocol of Peeters et al. ("Motilin receptor", Motilin, Z. Itoh, ed., Acad. Press, San Diego, pp 93–109 (1990). Motilin receptors were isolated from rabbit antral smooth muscle tissue. [$^{125}$I]-motilin is used as the ligand for the receptors. Binding of the test compound is expressed as the negative logarithm of the concentration of the test compound displacing 50% of bound [$^{125}$I]-motilin. The compound of Example 1 was found to have motilin binding with a $pK_d$=7.94. The $pK_d$ of motilin under similar conditions is 9.1, thus indicating that this compound binds strongly to motilin receptors. This ability of the compounds to bind strongly to motilin receptors and the effective absence of elicitation of contractile activity by estimated therapeutic concentration of these compounds in rabbit duodenal smooth muscle together constitute motilin antagonist activity of the compounds.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A compound having the Formula

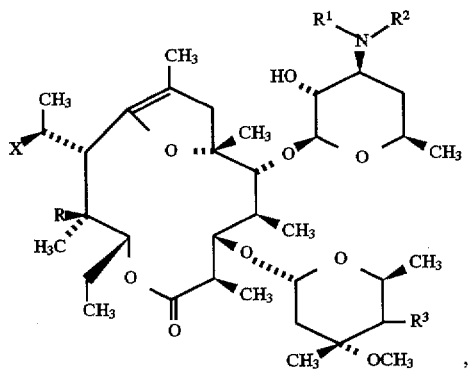

or a pharmaceutically acceptable salt thereof, wherein

R is H or OH;

$R^1$ and $R^2$ are independently selected from the group consisting of H, $C_1$-$C_8$-alkyl, phenyl-$C_1$-$C_8$-alkyl, and naphthyl-$C_1$-$C_8$-alkyl;

$R^3$ is selected from the group consisting of H, OH, O—$C_1$-$C_8$-alkyl, O—CO—$C_1$-$C_8$-alkyl, O—CO—phenyl, O—CO—$NR^4R^5$, where $R^4$ and $R^5$ are independently H or $C_1$-$C_8$-alkyl; $NH_2$; N—CO—$C_1$-$C_8$-alkyl; N—CO-phenyl; and N—CO—$NR^4R^5$, wherein $R^4$ and $R^5$ are independently H or $C_1$-$C_8$-alkyl; and X is selected from the group consisting of F, Cl, Br, and I.

2. A compound according to claim 1, wherein $R^1$ and $R^2$ are $C_1$-$C_8$-alkyl and $R^3$ is selected from the group consisting of H, OH, O—$C_1$-$C_8$-alkyl, O—CO—$NR^4R^5$, and $NH_2$, wherein $R^4$ and $R^5$ are independently H or $C_1$-$C_8$-alkyl.

3. A compound according to claim 1 selected from the group consisting of

Compound of Formula (I); R=H; $R^1$=methyl; $R^2$=; $R^3$=H; X=F;

Compound of Formula (I); R=OH; $R^1$=methyl; $R^2$=ethyl; $R^3$=H; X=F;

Compound of Formula (I); R=H; $R^1$=methyl; $R^2$=i-propyl; $R^3$=H; X=F;

Compound of Formula (I); R=H; $R^1$=methyl; $R^2$=phenylmethyl; $R^3$=H; X=F;

Compound of Formula (I); R=H; $R^1$=methyl; $R^2$=methyl; $R^3$=OH; X=F;

Compound of Formula (I); R=H; $R^1$=methyl; $R^2$=methyl; $R^3$=methoxy; X=F;

Compound of Formula (I); R=H; $R^1$=methyl; $R^2$=methyl; $R^3$=OCON(CH$_3$)$_2$; X=F;

Compound of Formula (I); R=H; $R^1$=methyl; $R^2$=methyl; $R^3$=NH$_2$; X=F; and Compound of Formula (I); R=H; $R^1$=methyl; $R^2$=methyl; $R^3$=H; X=Cl.

4. A compound according to claim 1, wherein R is H; $R^1$ and $R^2$ are $C_1$-$C_8$-alkyl, $R^3$ is H and X is F.

5. A compound according to claim 4 which is

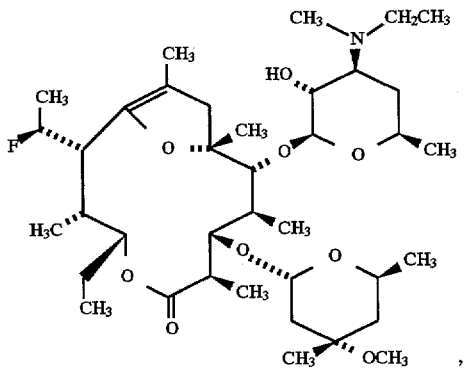

Compound of Formula (I); R=H; $R^1$=methyl; $R^2$=ethyl; $R^3$=H; X=F.

6. A pharmaceutical composition comprising a therapeutically effective amount of a compound according to claim 1 and a pharmaceutically acceptable carrier.

7. A pharmaceutical composition comprising a therapeutically effective amount of a compound according to claim 5 and a pharmaceutically acceptable carrier.

8. A method for treating gastrointestinal disorders associated with hypermotilinemia in humans and other mammals in need of such treatment comprising administering, to a patient in need thereof, a therapeutically effective amount of a compound according to claim 1.

9. A method for treating gastrointestinal disorders associated with hypermotilinemia in humans and other mammals in need of such treatment comprising administering, to a patient in need thereof, a therapeutically effective amount of a compound according to claim 5.

10. A process for the preparation of the compounds having the formula

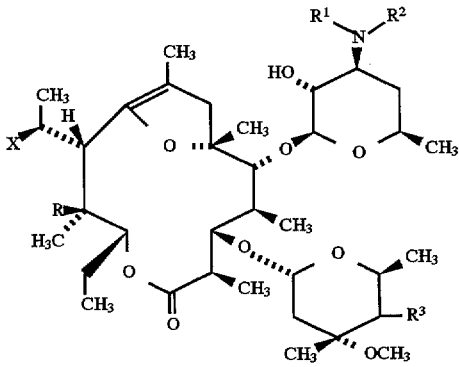

wherein

R is H or OH;

$R^1$ and $R^2$ are independently selected from the group consisting of H, $C_1$-$C_8$-alkyl, phenyl-$C_1$-$C_8$-alkyl, and naphthyl-$C_1$-$C_8$-alkyl;

$R^3$ is selected from the group consisting of H, OH, O—$C_1$-$C_8$-alkyl, O—CO-$C_1$-$C_8$-alkyl, O—CO-phenyl, O—CO—$NR^4R^5$, where $R^4$ and $R^5$ are independently H or $C_1$-$C_8$-alkyl; $NH_2$; N—CO—$C_1$-$C_8$-alkyl; N—CO-phenyl; N—CO—$NR^4R^5$, wherein $R^4$ and $R^5$ are independently H or $C_1$-$C_8$-alkyl; and X is selected from the group consisting of F, Cl, Br, or I;

the method comprising (a) selectively protecting the 2'-hydroxyl group of a compound having the formula

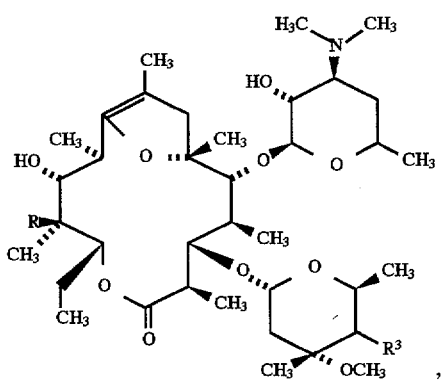

wherein $R^3$ is as described above, by treatment with a reagent selected from the group an acid anhydride and an acid halide under neutral aprotic conditions, and isolating the first intermediate compound having the formula

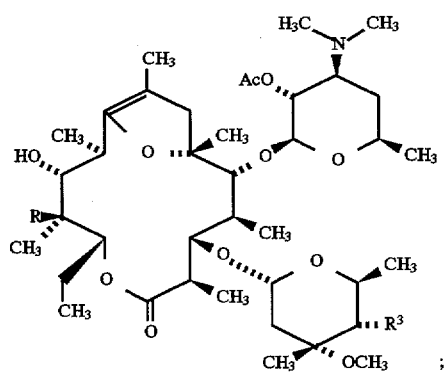

(b) ring-contracting the first intermediate compound by treatment with a reagent capable donating a nucleophilic halogen species, at ambient temperature and under an inert atmosphere, and isolating the 13-membered ring-contracted second intermediate compound having the formula

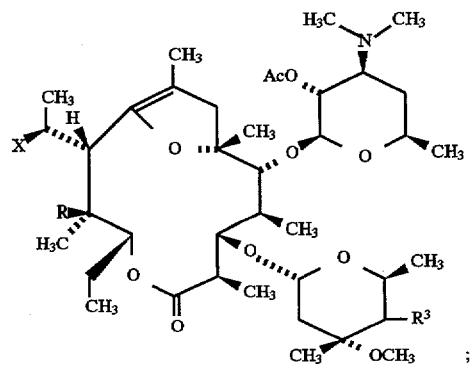

(c) optionally demethylating one or more of the 3'-N methyl groups by treatment with iodine in the presence of sodium acetate in a methanolic solution, followed by N-alkylation by treatment with a reagent selected from the group comprising an alkyl halide and hydrogen and a noble metal catalyst in the presence of an aldehyde or ketone and an alkali metal halide, and isolating the third intermediate compound having the formula

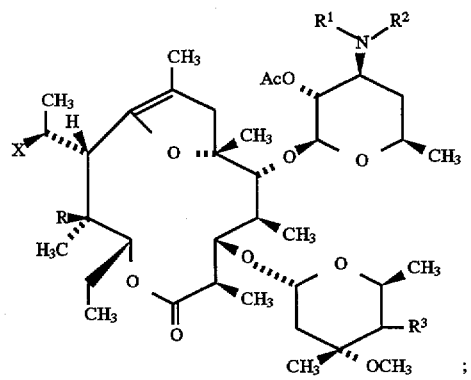

and (d) deprotecting the 2' hydroxyl protecting group by treatment with methanol.

11. A process according to claim 10, wherein X is F and in step (b) the reagent capable of donating a nucleophilic halogen species is diethylamidosulfur trifluoride (DAST).

12. A process for the preparation of the compound having the formula

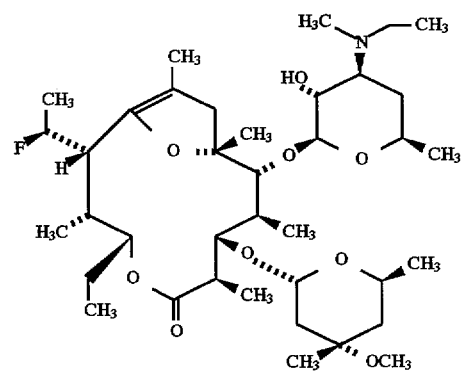

the method comprising (a) treating the compound having the formula

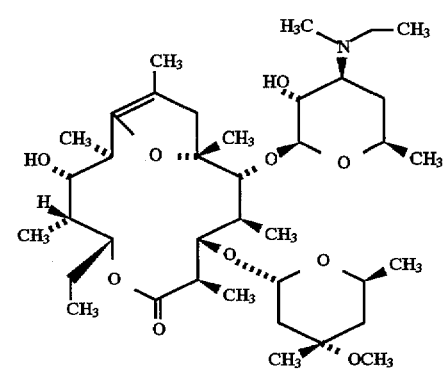

with acetic anhydride under $N_2$ at room temperature for 4 hours, and isolating the first intermediate compound having the formula

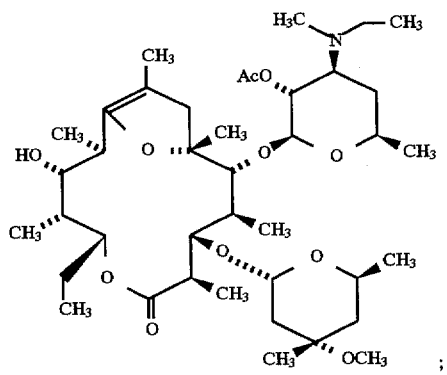
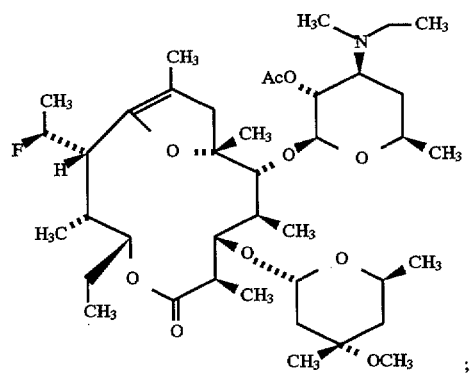
(b) ring-contracting the first intermediate compound by treatment with diethylamidosulfur trifluoride (DAST) under $N_2$ at room temperature for 4 hours, and isolating the second intermediate compound having the formula
(c) treating the second intermediate compound with methanol, and isolating the desired product.
* * * * *

UNITED STATES PATENT AND TRADEMARK OFFICE
CERTIFICATE OF CORRECTION

PATENT NO. : 5,712,253
DATED : January 27, 1998
INVENTOR(S) : Lartey et al.

It is certified that error appears in the above-identified patent and that said Letters Patent is hereby corrected as shown below:

Column 19, line 44, change "$R^2=$;" to --$R^2=H$;--.

Column 21, line 18, change "an acid" to --consisting of an acid--.

Signed and Sealed this

Twenty-sixth Day of May, 1998

Attest:

BRUCE LEHMAN

*Attesting Officer*  *Commissioner of Patents and Trademarks*